(12) United States Patent
Maeda et al.

(10) Patent No.: US 6,589,031 B2
(45) Date of Patent: Jul. 8, 2003

(54) TURBO BLOOD PUMP

(75) Inventors: Hiroyuki Maeda, Hiroshima (JP);
Masafumi Sato, Hiroshima (JP); Kenji Araki, Miyazaki (JP); Hirofumi Anai, Oita (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/952,086

(22) Filed: Sep. 13, 2001

(65) Prior Publication Data

US 2002/0076322 A1 Jun. 20, 2002

(30) Foreign Application Priority Data

Sep. 14, 2000 (JP) ........................................ 2000-279994

(51) Int. Cl.$^7$ ................................................ F04B 17/00
(52) U.S. Cl. ...................... 417/420; 415/206; 416/179; 600/16; 384/246
(58) Field of Search .......................... 417/420, 423.12, 417/423.13; 415/206, 900; 416/179, 183; 600/16; 384/245, 246

(56) References Cited

U.S. PATENT DOCUMENTS

| 2,810,349 | A | | 10/1957 | Zozulin |
| 3,411,450 | A | * | 11/1968 | Clifton ........................ 417/420 |
| 3,558,948 | A | | 1/1971 | Laing |
| 4,507,048 | A | * | 3/1985 | Belenger et al. .............. 415/90 |
| 4,984,972 | A | * | 1/1991 | Clausen et al. ............. 417/420 |
| 5,360,317 | A | * | 11/1994 | Clausen et al. ............. 415/206 |
| 5,399,074 | A | * | 3/1995 | Nose et al. ............... 417/423.1 |
| 5,458,459 | A | * | 10/1995 | Hubbard et al. ............ 415/206 |
| 5,803,720 | A | | 9/1998 | Ohara et al. ................ 417/420 |
| 5,863,179 | A | * | 1/1999 | Westphal et al. ........... 415/206 |
| 6,015,434 | A | | 1/2000 | Yamane |
| 6,030,188 | A | | 2/2000 | Nojiri et al. |
| 6,135,710 | A | * | 10/2000 | Araki et al. ................. 415/206 |

FOREIGN PATENT DOCUMENTS

| EP | 0 425 257 | 5/1991 |
| EP | 0 504 863 | 9/1992 |
| JP | 10-33664 | 2/1998 |
| JP | 10-99429 | 4/1998 |

* cited by examiner

Primary Examiner—Charles G. Freay
Assistant Examiner—John F Belena
(74) Attorney, Agent, or Firm—Merchant & Gould P.C.

(57) ABSTRACT

A turbo blood pump includes a housing 1 having a pump chamber 2, an inlet port 3, and an outlet port 4, an impeller 5 disposed rotatably in the pump chamber, an upper bearing 9 and a lower bearing 10 supporting the impeller rotatably, and a driving force transmitting unit for driving the impeller to rotate. The upper bearing is supported at a position in the pump chamber below the inlet port, so that a cross-sectional area of the pump chamber in a plane including an upper end of the upper bearing and being orthogonal to a shaft of the impeller is larger than a cross-sectional area of a flow path of the inlet port at a portion where the inlet port is coupled to the pump chamber, and thus obstruction with respect to blood flow by the upper bearing is of such a degree as to be permissible from a practical viewpoint, while an impeller is supported by upper and lower bearings. Thereby, the pump is less likely to cause problems of blood stagnation and thrombus formation.

3 Claims, 4 Drawing Sheets

TURBO BLOOD PUMP

BACKGROUND OF THE INVENTION

1. Field of the Invention

The present invention relates to a blood pump for transferring blood. More specifically, this invention relates to a turbo blood pump in which centrifugal force generated by rotation of an impeller causes blood to flow.

2. Related Background Art

Blood pumps are indispensable to an artificial heart lung apparatus or the like for extracorporeal blood circulation. Among blood pumps, turbo blood pumps have been dominant. A turbo blood pump has a structure that is described as follows: a housing in which a pump chamber is formed includes an inlet port for introducing blood in a center portion and an outlet port for discharging blood in an outer peripheral portion; an impeller is disposed in the pump chamber, and rotation of the impeller causes blood to flow.

FIG. 5 shows a turbo blood pump as an example that is currently under development by the inventors of the present invention. In FIG. 5, a reference numeral 21 denotes a housing that includes an inlet port 21a and an outlet port (not shown). In the housing 21, a pump chamber 22 is formed and an impeller 23 is provided. The impeller 23 is supported rotatably by an upper bearing 24 and a lower bearing 25. In a concave portion 21b provided in a lower center of the housing 21, a rotor 26 is provided. Although not shown in the figure, the rotor 26 is connected to a motor and driven to rotate by the motor. In a lower and outer portion of the impeller 23, driven magnets 27 are provided in such a manner as to be positioned on an inner side of a side wall of the concave portion 21b of the housing 21. The rotor 26 is provided with driving magnets 28 in such a manner that the driving magnets 28 are positioned on an outer side of the side wall of the concave portion 21b. Accordingly, through magnetic attraction in a radial direction acting between the driven magnets 27 and the driving magnets 28, rotation of the rotor 26 is transmitted to the impeller 23. By rotation of the impeller 23, blood in the pump chamber 22 flows to be discharged from the outlet port. In accordance with this, blood is introduced from the inlet port 21a and thus blood flow is formed.

A blood pump is required not to cause thrombus formation, which is one of the specifications required for a blood pump. The presence of a structural member that obstructs a flow path in a blood pump causes blood stagnation and thereby is likely to induce thrombus formation. In the blood pump shown in FIG. 5, the upper bearing 24 is disposed in the inlet port 21a. The upper bearing 24 is positioned in the inlet port 21a that is comparatively narrow as a flow path, thereby considerably obstructing blood flow. Particularly, when a thick support 29 is provided so that the strength of a bearing portion is increased, the obstruction with respect to blood flow can be quite large.

In order to solve the aforementioned problem, an example is described in JP10(1998)-33664A that has a structure in which a shaft equipped with vanes of an impeller is made hollow so that a hollowed-out portion is used as a flow path. The outer periphery of the hollow shaft is supported by a magnetic bearing. This structure allows the hollowed-out portion to be free from a portion that obstructs blood flow. However, the hollow shaft is required to be relatively long and large in diameter, thereby being disadvantageous in making a device reduced in size and less complicated. For example, a blood pump for use with children has an inlet port with a diameter of about 6 mm. In this case, the structure described in JP10(1998)-33664A hardly can be adopted.

It also may be possible to solve the aforementioned problem by employing a structure in which an impeller is supported only by a bearing disposed in a lower portion of the impeller, so that an upper bearing is not required. However, supporting by a lower bearing alone is likely to cause instability of the rotation of an impeller. Particularly, in a structure in which rotation of a motor is transmitted to an impeller through magnetic coupling, it is desirable in terms of safety that the impeller be supported by two bearings disposed in upper and lower portions.

SUMMARY OF THE INVENTION

It is an object of the present invention to provide a turbo blood pump, in which an impeller is supported by upper and lower bearings, while obstruction to blood flow formed by the upper bearing is reduced, thereby being less likely to cause problems in terms of blood stagnation and thrombus formation.

The turbo blood pump of the present invention includes a housing having a pump chamber, an inlet port, and an outlet port, an impeller disposed rotatably in the pump chamber, upper and lower bearings supporting the impeller rotatably, and a driving force transmitting unit for driving the impeller to rotate. The upper bearing is supported at a position in the pump chamber below the inlet port, and the position is determined so that a cross-sectional area of the pump chamber in a plane including an upper end of the upper bearing and being orthogonal to a shaft of the impeller is larger than a cross-sectional area of a flow path of the inlet port at a portion where the inlet port is coupled to the pump chamber, and thus any obstruction to blood flow caused by disposing the upper bearing is of such a degree as to be permissible from the practical viewpoint.

According to this configuration, obstruction with respect to blood flow by an upper bearing is of such a degree as to be permissible, whereby a turbo blood pump is provided that is less likely to cause problems in terms of blood stagnation and thrombus formation.

In this configuration, preferably, the upper bearing is positioned in such a manner that a cross-sectional area $S_B$ of the pump chamber at a position of the upper end of the upper bearing satisfies the relationship, $2.32 \times S_A \leq S_B \leq 7.50 \times S_A$, with respect to a cross-sectional area $S_A$ of the inlet port at the portion where the inlet port is coupled to the pump chamber.

Furthermore, a configuration may be possible in which a plurality of bearing supports are fixed at a first end to a lower end of the inlet port and extend toward the pump chamber to support the upper bearing by a second end thereof.

Furthermore, the aforementioned configuration is effective in a turbo blood pump having a configuration in which the driving force transmitting unit includes driving magnets provided on a rotor disposed on an outer side of the housing, the rotor is rotatably driven by a motor, and driven magnets provided on the impeller, and the driven magnets and the driving magnets are opposed to each other with a wall of the housing being interposed between them to form a magnetic coupling for transmitting rotation of the rotor to the impeller.

In the case described above, a configuration may be possible in which the driven magnets and the driving magnets are disposed so that a direction of the magnetic coupling based on attraction acting between the driven magnets and the driving magnets is inclined with respect to a rotary shaft of the impeller.

DETAILED DESCRIPTION OF THE INVENTION

Figure 1:
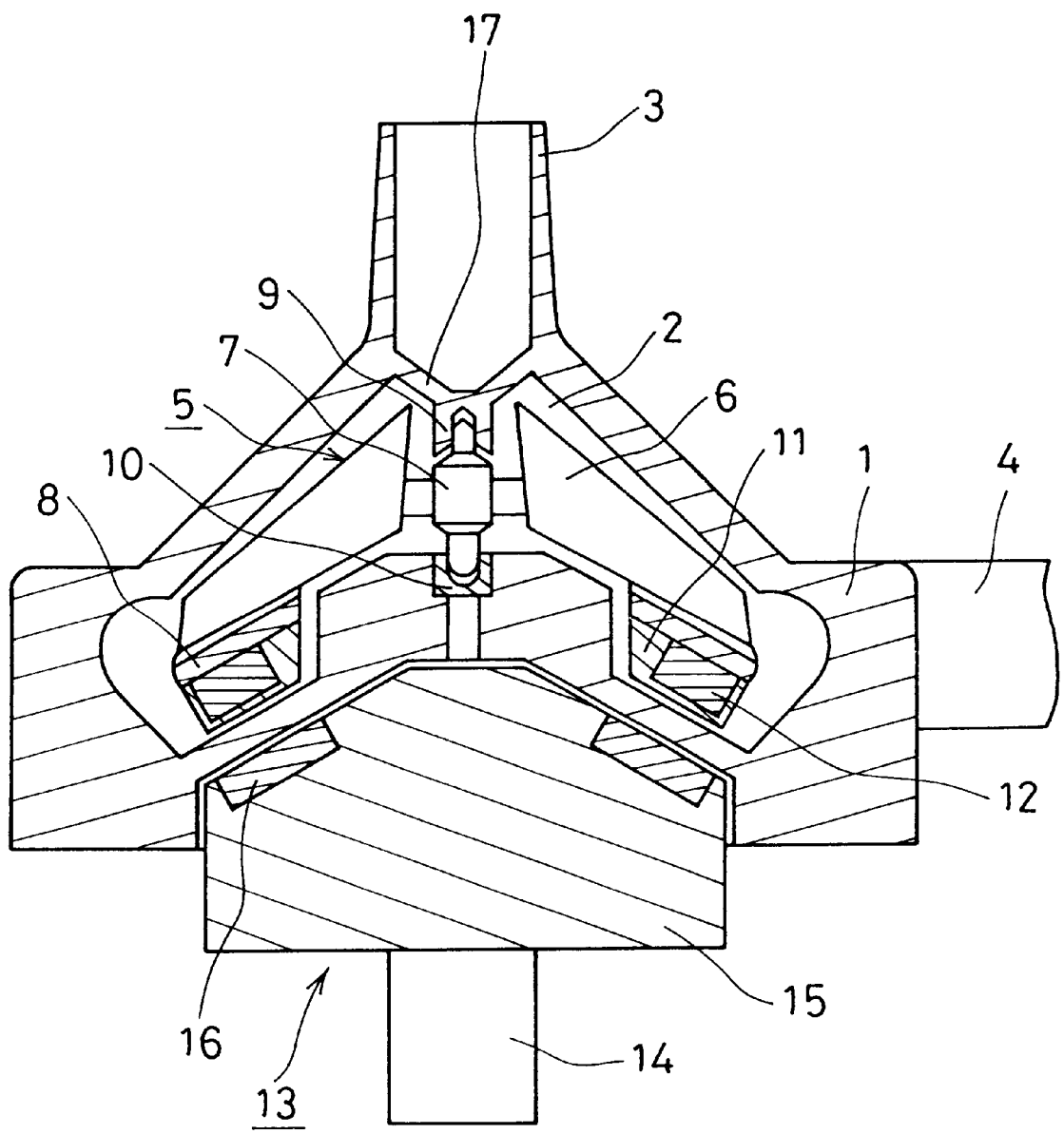
FIG. 1 is a cross-sectional view showing a turbo blood pump of an embodiment according to the present invention.

FIG. 1 is a cross-sectional view showing a turbo blood pump of an embodiment according to the present invention. In FIG. 1, a reference numeral 1 denotes a housing that includes a pump chamber 2 for allowing blood to pass therethrough and flow. The housing 1 is provided with an inlet port 3 that communicates with an upper portion of the pump chamber 2 and an outlet port 4 that communicates with a side portion of the pump chamber 2. In the pump chamber 2, an impeller 5 is disposed. The impeller 5 includes six vanes 6, a rotary shaft 7, and an annular connection member 8 having a ring-like shape. The vanes 6 are coupled to the rotary shaft 7 on a side of a center portion and to the annular connection member 8 on a side of a peripheral portion. The rotary shaft 7 is supported rotatably by an upper bearing 9 and a lower bearing 10 that are provided in the housing 1. In the annular connection member 8, a magnet case 11 is provided in which driven magnets 12 are embedded and secured. The respective driven magnets 12 have a cylindrical shape and six of them are spaced at a uniform distance from each other in a peripheral direction with respect to the annular connection member 8.

Figure 2A:
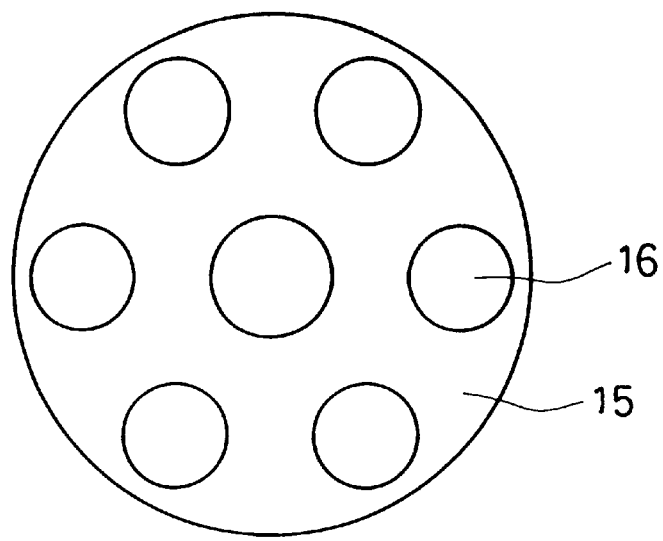
FIGS. 2A and 2B are a plan view and a front view, respectively, showing a rotor used in the turbo blood pump shown in FIG. 1.

In a lower portion of the housing 1, a rotor 13 is disposed that includes a driving shaft 14 and a magnetic coupling part 15 substantially having a cylindrical shape. The driving shaft 14 and the magnetic coupling part 15 are coupled to each other. Although not shown in the figure, the driving shaft 14 is supported rotatably and connected to a source of driving force such as a motor to be driven to rotate. Further, although not shown in the figure, the rotor 13 and the housing 1 are connected to each other in such a manner as to maintain a constant positional relationship between them. In an upper face portion of the magnetic coupling part 15, driving magnets 16 are embedded and secured. As shown in FIG. 2A showing a plan view of the rotor 13, the respective driving magnets 16 have a cylindrical shape and six of them are spaced at a uniform distance from each other in a peripheral direction.

The driving magnets 16 are disposed so as to oppose the respective driven magnets 12 with a wall of the housing 1 being interposed between them. Accordingly, the rotor 13 and the impeller 5 are in a state where they are coupled magnetically to each other. Thus, rotation of the rotor 13 causes the impeller 5 to be driven to rotate through the magnetic coupling.

Figure 3:
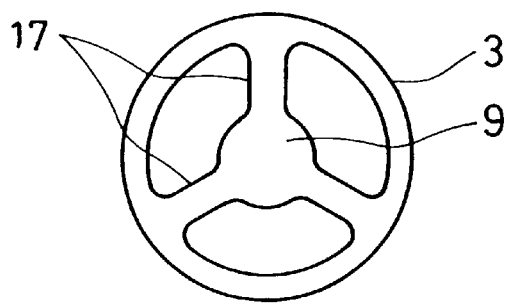
FIG. 3 is an enlarged plan view showing an upper bearing used in the turbo blood pump shown in FIG. 1.

The upper bearing 9 is disposed in a position below the inlet port 3 and within the pump chamber 2. FIG. 3 is an enlarged plan view showing the upper bearing 9. As shown in FIG. 3, three bearing supports 17 are used, and the respective bearing supports 17 extend in a radial direction and support the upper bearing 9 in a center portion of a cross section of a flow path. As shown in FIG. 1, one end of each bearing support 17 is fixed on an inner face of a lower end of the inlet port 3, and the other end thereof extends downward diagonally and enters into the pump chamber 2 to support the upper bearing 9.

Figure 4:
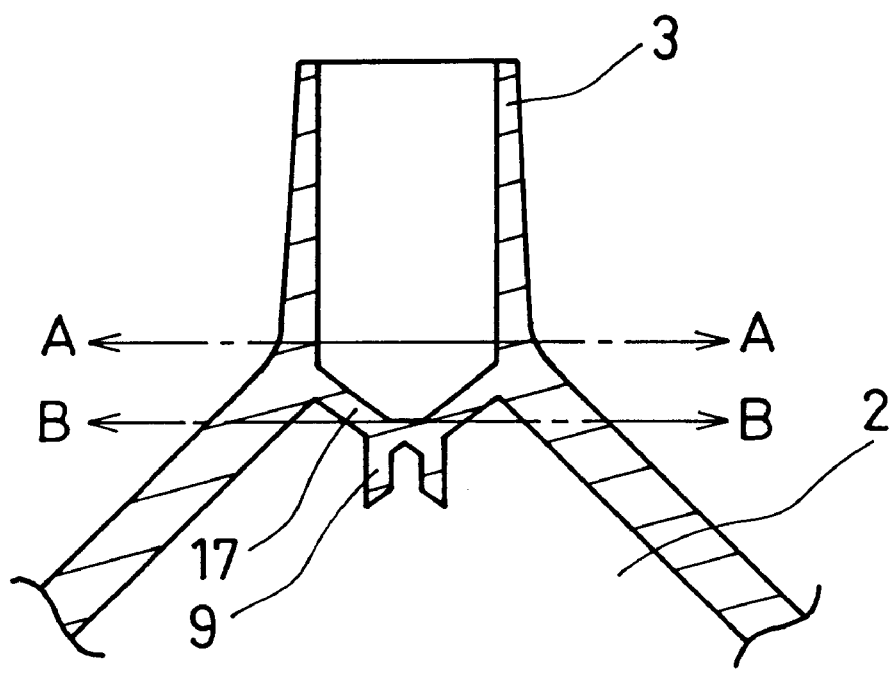
FIG. 4 is a schematic diagram for explaining the setting of a position where the upper bearing is supported in the turbo blood pump shown in FIG. 1.

For convenience, a cross-sectional area of a flow path of the inlet port 3 in a portion where the inlet port 3 and the pump chamber 2 are coupled to each other, namely, a cross-sectional area of a flow path in a cross section A—A shown in FIG. 4 is represented by $S_A$. A cross-sectional area of a flow path in a position where the upper bearing 9 is disposed, namely, a cross-sectional area of a flow path in a cross section B—B shown in FIG. 4 is represented by $S_B$. In other words, the cross-sectional area $S_B$ of a flow path means a cross-sectional area of the pump chamber 2 at the position of the upper end of the upper bearing 9. It should be noted that the cross-sectional area $S_B$ is defined herein as the area in the cross section B—B when the upper bearing 9 and the bearing supports 17 are not present.

According to a supporting structure of the upper bearing 9 as described above, the cross-sectional area $S_B$ of a flow path is sufficiently large compared with the cross-sectional area $S_A$ of a flow path. Therefore, a sufficiently large area of a blood flow path can be secured after providing the upper bearing 9 and the bearing supports 17. As a result of this, any obstruction to blood flow caused by providing the upper bearing 9 is reduced to such a degree as to be permissible from the practical viewpoint. That is, the upper bearing 9 and the bearing supports 17 are positioned in a portion having an enlarged cross-sectional area of a flow path compared with that of the inlet port 3, so that obstruction to blood flow caused around an inlet of the pump chamber 2 is of such a degree as to be acceptable. Obviously, the degree of obstruction to blood flow caused by the presence of the bearing supports 17 is too small to matter compared with that in the case where the upper bearing 9 is positioned in the inlet port 3.

As described above, the upper bearing 9 is disposed in a position of a flow path in the pump chamber 2 having a sufficiently large cross-sectional area. The sufficiently large cross-sectional area of a flow path is defined as an area larger than a cross-sectional area of a flow path of the inlet port 3, so that obstruction with respect to blood flow is reduced to such a degree as to be permissible from the practical viewpoint.

As a condition of setting a position where the upper bearing 9 is supported, it is practically suitable that the cross-sectional area SB has a value within the range satisfying the following relationship with respect to the cross-sectional area $S_A$: $2.32 \times S_A \leq S_B \leq 7.50 \times S_A$. That is, a position where the upper bearing 9 is supported should be determined so that the cross-sectional area $S_B$ falls within the range satisfying the foregoing relationship. When the position is determined so that the cross-sectional area $S_B$ is below the lower limit, blood flow suffers obstruction. On the other hand, when the position is set so that the cross-sectional area $S_B$ is above the upper limit, the upper bearing 9 and the lower bearing 10 are positioned so close to each other that it is difficult to support the impeller 5 adequately.

Preferable results were obtained when the cross-sectional area $S_B$ and the cross-sectional area $S_A$ were within the range satisfying the following relationship: $2.58 \times S_A \leq S_B \leq 4.45 \times S_A$.

In one example of a pump for use with a child, $S_A$ was 28 mm$^2$ (radius of 3 mm), $S_B$ was 126 mm$^2$ (radius of 6.33 mm)

and a cross-sectional area of the upper bearing 9 at the upper end was 9.6 mm² (radius of 1.75 mm). In one example of a pump for use with an adult, $S_A$ was 57 mm² (radius of 4.25 mm), $S_B$ was 147 mm² (radius of 6.83 mm) and a cross-sectional area of the upper bearing 9 at the upper end was 9.6 mm² (radius of 1.75 mm).

The range described above in connection with the cross-sectional area $S_B$ depends on dimensions of the upper bearing 9 and the bearing supports 17. However, as long as the dimensions are within the range of values suitable for practical use, the range described above can be applicable for achieving a practical effect without any change being required.

As shown in FIG. 1, a surface of the annular connection member 8 on which the driven magnets 12 are provided is not orthogonal to the rotary shaft 7 but inclined at a predetermined angle. Likewise, an upper surface of the magnetic coupling part 15 on which the driving magnets 16 are provided is inclined. Thus, the driven magnets 12 and the driving magnets 16 are coupled magnetically on a plane inclined with respect to the rotary shaft of the impeller 5.

As described above, by making the plane on which magnetic coupling is formed inclined, magnetic attraction between the impeller 5 and the rotor 13 acts in a direction inclined with respect to the rotary shaft of the impeller 5. As a result of this, a load imposed downward on the lower bearing 10 is reduced, and thus abrasion of the lower bearing 10 is eased, thus permitting the magnetic coupling to be made sufficiently strong. The bearing structure of the present invention is suitable in the case where a driving force transmission system employing magnetic coupling is used. This is because in the case of employing magnetic coupling, it is required to use the upper and lower bearings as a set in consideration of safe supporting of the impeller 5, while suppressing obstruction with respect to blood flow.

Figure 5:
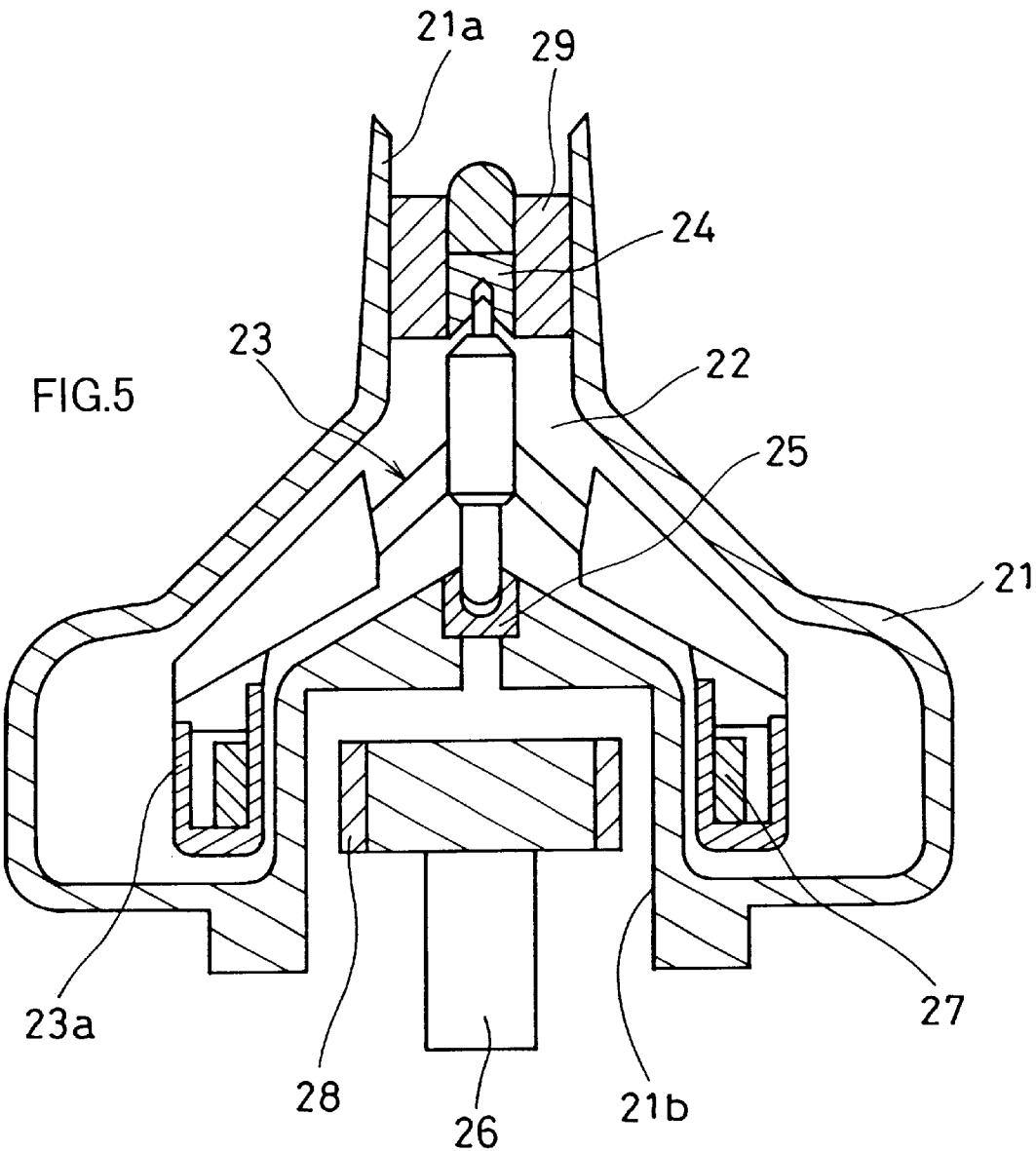
FIG. 5 is a cross-sectional view showing an example of another turbo blood pump.

By disposing the driven magnets 12 and the driving magnets 16 on the inclined planes, a large area can be provided easily for a portion in which the driven magnets 12 and the driving magnets 16 are opposed to each other without increasing a size of an outer peripheral surface of the annular connection member 8 in a direction of the shaft, compared with the configuration shown in FIG. 5 in which magnetic attraction acts in a radial direction. Accordingly, a surface area of a most outer peripheral portion contacting blood at a high peripheral velocity is reduced, whereby hemolysis is less likely to occur. Further, a blood stagnation portion formed between an inner peripheral surface of the annular connection member 8 and an inner side surface of the housing 1 also is reduced in size, whereby thrombus formation is suppressed.

Figure 2B:
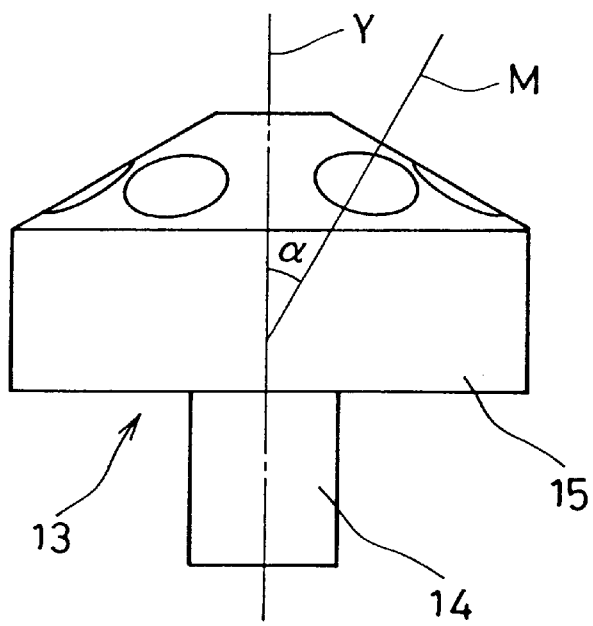

A direction of magnetic coupling is denoted by a line M orthogonal to an upper inclined face of the magnetic coupling part 15 in FIG. 2B. In FIG. 2B, a line Y denotes a rotation axis. An angle formed by the line M showing a direction of magnetic coupling with respect to the line Y showing the rotation axis is set to a value in the range of 30°±15°. When the value falls within this range, the effects described above can be obtained without entailing problems. When the value is above this range, a problem in connection with magnetic coupling in a radial direction is caused. That is, a surface area of the outer peripheral portion rotating at a high peripheral velocity is increased, which is undesirable. On the other hand, when the value is below this range, a problem in connection with magnetic coupling in a vertical direction is caused. That is, a load imposed on the lower bearing 10 is increased, which is undesirable.

Preferably, the inclined surface is formed in such a manner that the magnetic coupling portion 15 of the rotor 13 has a shape narrowed upward as a frustoconical member. This allows a space formed between the inclined face and the impeller 5 to be reduced in size, thereby being effective in miniaturization of the pump.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A turbo blood pump, comprising:
   a housing having a pump chamber, an inlet port, and an outlet port;
   an impeller disposed rotatably in the pump chamber;
   upper and lower bearings supporting the impeller rotatably; and
   a driving force transmitting unit for driving the impeller to rotate,
   wherein the upper bearing is supported at a position in the pump chamber below the inlet port, the position being determined so that a cross-sectional area of the pump chamber in a plane including an upper end of the upper bearing and being orthogonal to a shaft of the impeller is larger than a cross-sectional area of a flow path of the inlet port at a portion where the inlet port is coupled to the pump chamber, so that an obstruction of blood flow by the upper bearing is of such a degree as to be permissible from a practical viewpoint,
   wherein a plurality of bearing supports are fixed at a first end to a lower end of the inlet port and extend toward the pump chamber to support the upper bearing by a second end thereof, and
   wherein a shaft of the impeller has a small diameter portion at an upper end, the upper bearing has a bore at a lower end, and the small diameter portion is inserted into the bore so that the upper portion of the shaft is supported and positioned by the upper bearing, and
   wherein the shaft has a slant surface formed by varying the diameter gradually at the boundary between the small diameter portion and the other larger diameter portion, and the end surface around the bore of the upper bearing has a shape corresponding to the slant surface of the shaft, so that the slant surface of the shaft is in contact with the end surface around the bore.

2. The turbo blood pump according to claim 1,
   wherein the driving force transmitting unit includes driving magnets provided on a rotor disposed on an outer side of the housing, the rotor is rotatably driven by a motor, and driven magnets provided on the impeller, and
   the driven magnets and the driving magnets are opposed to each other with a wall of the housing being interposed between them to form a magnetic coupling for transmitting rotation of the rotor to the impeller.

3. The turbo blood pump according to claim 2,
   wherein the driven magnets and the driving magnets are disposed so that a direction of the magnetic coupling based on attraction acting between the driven magnets and the driving magnets is inclined with respect to a rotary shaft of the impeller.

* * * * *